(12) United States Patent
Carney et al.

(10) Patent No.: US 12,268,626 B2
(45) Date of Patent: Apr. 8, 2025

(54) COMFORT HARNESS FOR ORTHOTIC BRACE

(71) Applicant: Orthocare Medical Equipment, LLC, Manchester, NH (US)

(72) Inventors: Rita Carney, Auburn, NH (US); Steve Santaniello, Milford, NH (US)

(*) Notice: Subject to any disclaimer, the term of this patent is extended or adjusted under 35 U.S.C. 154(b) by 352 days.

(21) Appl. No.: 18/085,826

(22) Filed: Dec. 21, 2022

(65) Prior Publication Data

US 2023/0123217 A1    Apr. 20, 2023

Related U.S. Application Data

(63) Continuation-in-part of application No. 16/830,353, filed on Mar. 26, 2020, now abandoned.

(60) Provisional application No. 62/823,795, filed on Mar. 26, 2019.

(51) Int. Cl.
*A61F 5/37* (2006.01)

(52) U.S. Cl.
CPC .................. *A61F 5/3738* (2013.01)

(58) Field of Classification Search
CPC ...... A61F 5/00; A61F 5/01; A61F 5/04; A61F 5/05; A61F 5/058; A61F 5/025; A61F 5/0102; A61F 5/0104; A61F 5/0118; A61F 5/05858; A61F 5/30; A61F 5/37; A61F 5/373; A61F 5/3715; A61F 5/3723; A61F 5/3738; A61F 5/3761; A62B 35/0018; A41F 15/007

See application file for complete search history.

(56) References Cited

U.S. PATENT DOCUMENTS

| | | | |
|---|---|---|---|
| 4,598,703 A | 7/1986 | Lindemann | |
| 4,905,713 A | 3/1990 | Morante | |
| 5,411,541 A | 5/1995 | Bell | |
| 5,695,452 A | 12/1997 | Grim | |
| 6,659,971 B2 | 12/2003 | Gaylord | |
| 7,563,236 B2 | 7/2009 | Kazmierczak et al. | |
| 8,414,512 B2 | 4/2013 | Fout | |
| 2003/0186619 A1* | 10/2003 | Falla | A41F 15/007 450/86 |
| 2004/0065272 A1* | 4/2004 | Reynolds | A62B 35/0018 119/770 |
| 2007/0106187 A1* | 5/2007 | Campbell | A61F 5/3723 602/19 |
| 2007/0167895 A1 | 7/2007 | Gramza | |
| 2012/0197160 A1* | 8/2012 | Reinhardt | A61F 5/026 600/587 |
| 2015/0157488 A1 | 6/2015 | Grunden et al. | |
| 2016/0113406 A1 | 4/2016 | Shamaiengar | |

* cited by examiner

*Primary Examiner* — Ophelia A Hawthorne
*Assistant Examiner* — Gina McCarthy
(74) *Attorney, Agent, or Firm* — KPIP Law, PLLC; Kimberly A Peaslee

(57) ABSTRACT

A comfort harness for an orthotic brace being fully adjustable and having a crescent-shaped pad located about the front shoulder of a user for dispersing a load and for added comfort for the user. Multiple straps are provided for upper back, under arm, and cross-body support for the user. The comfort harness configured to connect with a variety of orthotics for an arm, a shoulder, and the like. In some cases, the comfort harness is capable of being donned and adjusted by the user when in a supine position.

20 Claims, 7 Drawing Sheets

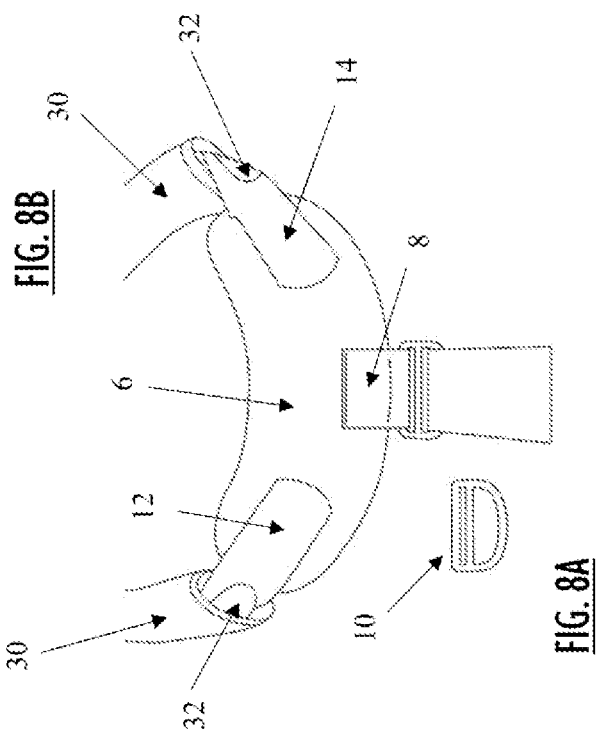
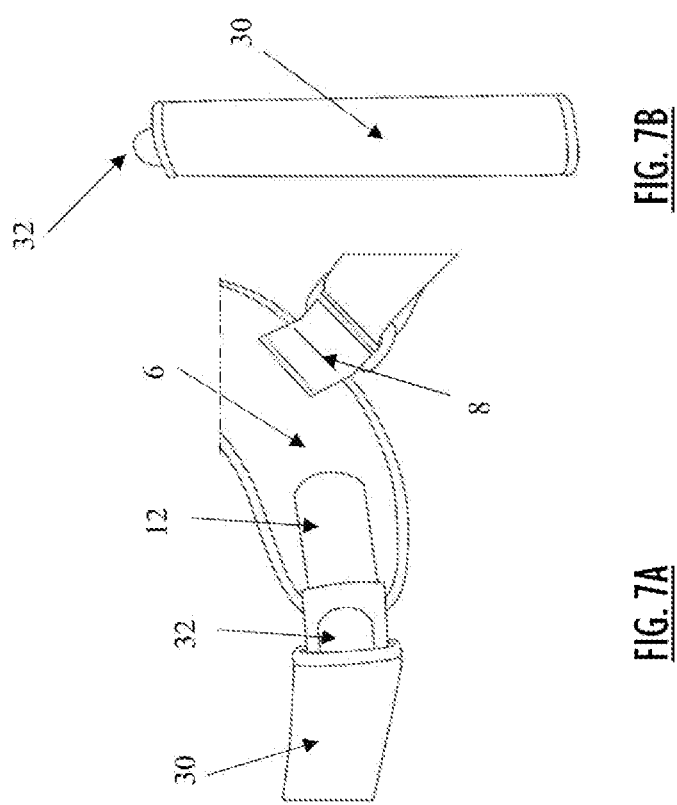

COMFORT HARNESS FOR ORTHOTIC BRACE

CROSS-REFERENCE TO RELATED APPLICATIONS

This application is a Continuation-in-Part of U.S. patent application Ser. No. 16/830,353, filed Mar. 26, 2020, which claims the benefit of U.S. Provisional Patent Application 62/823,795, filed Mar. 26, 2019, entitled "COMFORT HARNESS FOR ORTHOTIC BRACE" the content of each of which are incorporated by reference herein in their entirety.

FIELD OF THE DISCLOSURE

The present disclosure relates comfort harnesses for use with orthotics that provide for increased comfort and adjustability when donned by a user and provide for donning the comfort harness when a user is in a supine position.

BACKGROUND OF THE DISCLOSURE

Conventional orthotics have a single straight strap or pad that lays directly over the shoulder of a user. These pads do not conform to the anatomy of the user and typically pull downwards against the body and neck region causing discomfort and pain. This increase in pain and discomfort adds to the suffering of a patient already dealing with an injury.

One prior orthotic has three straps meeting at a frontal pad. However, the three connections are all fixed and non-adjustable, and the pad is square shaped such that the strap connecting down to the front of the orthotic does not allow for any rotation. Additionally, all three straps connect to a central ring and apply unwanted pressure against a single point on the body increasing discomfort. The straps also move independently on the ring causing excessive movement and rotation and chafing for the user. Finally, all three of the intersecting straps meet at a connector ring—a closed loop formed by the support straps is passed around an extended arm of a user and towards the patient's torso which creates a major fitting issue. Essentially, this requires the injured user to sliding their arm through the strap assembly as opposed to having the assembly wrap around the user from front to back as in the present solution.

While some prior systems may alleviate some neck pull, the single strap approach still crosses over the shoulder of the user to a sling in the front of the user's torso. There, a back connector has strap running vertical down towards a belt (about a waist of the user) and across to a sling. As weight is applied to the single strap orthotics, over the shoulder, the belt wants to rise up on the user's back creating discomfort and ill-fitting. Force is only applied to one section of the user's shoulder and does not distribute the load evenly.

Other systems attempt to alleviate shifting of the sling unit, but those single strap orthotics still go over the shoulder of the user and a second strap goes under the arm of the user but comes around to the back portion of the orthotic unit. The single strap does not diffuse the load and does not disperse load on the sling. Instead these orthotics are used to stop rotation of the sling. Regardless, these conventional systems do not have adjustability at the section attached to the shoulder. The three straps are all fixed directly to a single pad. Adjustment happens only at the lower sling and around the back lower sling and pillow. Thus, a user cannot release the harness away from their shoulder without moving away from a chair or a bed.

Wherefore it is an object of the present disclosure to overcome the above-mentioned shortcomings and drawbacks associated with the conventional harnesses for orthotic braces.

SUMMARY OF THE DISCLOSURE

The present disclosure overcomes several problems with conventional orthotics by providing a frontally removable and adjustable harness with a crescent shaped pad having specific connectivity and dimensions allowing for donning of the harness when a user is in a supine position. The single pad anatomically contours and disperses the load across the front of the chest and shoulder region.

One general aspect includes a comfort harness for an orthotic. The comfort harness also includes a single pad. The harness also includes an upper rounded end portion located between a user's neck and a user's shoulder when worn. The harness also includes a middle portion located over a user's pectoral muscle when worn supporting a fixed ring, the fixed ring being configured to connect to at least one cross-body strap. The harness also includes a lower rounded end portion located proximal to a user's arm pit when worn. The harness also includes a pair of parallel curves extending between the upper rounded portion and the lower rounded portion such that the single pad has an equal width from end to end, a first parallel curve forming a convex edge located adjacent a user's chest when worn, and a second parallel curve forming a concave edge located spaced away from a user's shoulder when worn. The harness also includes the upper rounded end portion reversibly attachable to an upper back strap and the lower rounded end portion reversibly attachable to an under arm strap. The single pad may include a single top layer facing away from a user's body when worn; a single bottom layer facing toward a user's body when worn, the single bottom layer being sized and shaped to match the top layer; and a rigid single middle layer that is sandwiched between the single top layer and the single bottom layer. The harness also includes a multi-strap connector located on a back of a user when worn having two or more slots for receiving and orienting straps and reversibly attachable to the upper back strap and the under arm strap. The harness also includes the at least one cross-body strap being reversibly attachable to an orthotic.

Implementations may include one or more of the following features. The comfort harness where the at least one cross-body strap may include a first and a second cross-body strap. The first cross-body strap is reversibly attached to the fixed ring on the single pad and reversibly attached to the orthotic. The second cross-body strap is permanently attached to the multi-strap connector and reversibly attached to the orthotic. The single pad further may include cooling fabric. The comfort harness may include at least one strap pad sized to fit around the upper back strap and/or the under arm strap. The at least one strap pad is a pair of strap pads each made of foam laminate and having a tab for reversibly securing to the single pad.

One general aspect includes an adjustable comfort harness for an orthotic. The adjustable comfort harness also includes a single pad. The harness also includes an upper rounded end portion located between a user's neck and a user's shoulder when worn. The harness also includes a middle portion supporting a fixed ring located over a user's pectoral muscle when worn. The harness also includes a lower rounded end portion located proximal to a user's arm pit when worn. The harness also includes a pair of parallel curves such that the single pad has an equal width from end to end, a first parallel curve forming a convex edge located adjacent a user's chest when worn, and a second parallel curve forming a concave edge located spaced away from a user's shoulder when worn. The harness also includes the upper rounded end portion reversibly attachable to an upper back strap and the lower rounded end portion reversibly attachable to an under arm strap. The harness also includes the single pad which may include: a single top layer of loop laminate facing away from a user's body when worn, a single bottom layer facing toward a user's body when worn, and a single middle layer enclosed within the single top layer and the single bottom layer to reinforce the single pad and prevent distortion when the harness is under tension. The harness also includes a multi-strap connector may include at least two slots for receiving straps, the multi-strap connector reversibly attachable to at least the upper back strap and the under arm strap. The harness also includes where a first cross-body strap is reversibly attached to the fixed ring on the single pad and reversibly attached to an orthotic and a second cross-body strap is reversibly attachable to the orthotic.

Implementations may include one or more of the following features. The comfort harness where the orthotic is a sling. The second cross-body strap is permanently attached to the multi-strap connector and reversibly attached to the orthotic. The single pad further may include cooling fabric. The comfort harness may include at least one strap pad sized to fit around the upper back strap and/or the under arm strap. The at least one strap pad is a pair of strap pads each made of foam laminate and having a tab for reversibly securing to the single pad.

One general aspect includes a comfort harness for an arm orthotic. The comfort harness also includes a single pad having an upper rounded end portion located between a user's neck and a user's shoulder when worn, a middle portion having a fixed ring for receiving a first cross-body strap and located over a user's pectoral muscle when worn, a lower rounded end portion located proximal to a user's arm pit when worn. The harness also includes a pair of parallel curves such that the single pad has an equal width from end to end, a first parallel curve forming a convex edge located adjacent a user's chest when worn, and a second parallel curve forming a concave edge located spaced away from a user's shoulder when worn. The harness also includes the upper rounded end portion being reversibly attachable to an upper back strap and the lower rounded end portion reversibly attachable to an under arm strap. The harness also includes the single pad may include: a top layer may include loop laminate facing away from a user's body when worn, a bottom layer may include foam laminate facing toward a user's body when worn, and a rigid single middle layer that is sandwiched between the top layer and the bottom layer to prevent distortion when the harness is under tension. The harness also includes a multi-strap connector having two or more slots for receiving and orienting straps on a back of the user and reversibly attachable to the upper back strap and the under arm strap.

Implementations may include one or more of the following features. The comfort harness where the first cross-body strap is reversibly attached to the fixed ring on the single pad and reversibly attached to the arm orthotic. The comfort harness may include a second cross-body strap permanently attached to the multi-strap connector and reversibly attached to the arm orthotic. The single pad further may include cooling fabric. The comfort harness may include at least one strap pad sized to fit around the upper back strap and/or the under arm strap. The at least one strap pad is a pair of strap pads each made of foam laminate and having a tab for reversibly securing to the single pad.

These aspects of the disclosure are not meant to be exclusive and other features, aspects, and advantages of the present disclosure will be readily apparent to those of ordinary skill in the art when read in conjunction with the following description, appended claims, and accompanying drawings.

BRIEF DESCRIPTION OF THE DRAWINGS

The foregoing and other objects, features, and advantages of the disclosure will be apparent from the following description of particular implementations of the disclosure, as illustrated in the accompanying drawings in which like reference characters refer to the same parts throughout the different views. The drawings are not necessarily to scale, emphasis instead being placed upon illustrating the principles of the disclosure.

FIG. 7A and FIG. 7B show perspective views of one implementation of the comfort harness for an orthotic brace having strap pads according to the principles of the present disclosure.

FIG. 8A and FIG. 8B show perspective views of one implementation of the comfort harness for an orthotic brace having strap pads and a fixed ring according to the principles of the present disclosure.

DETAILED DESCRIPTION OF THE DISCLOSURE

Figure 1B:
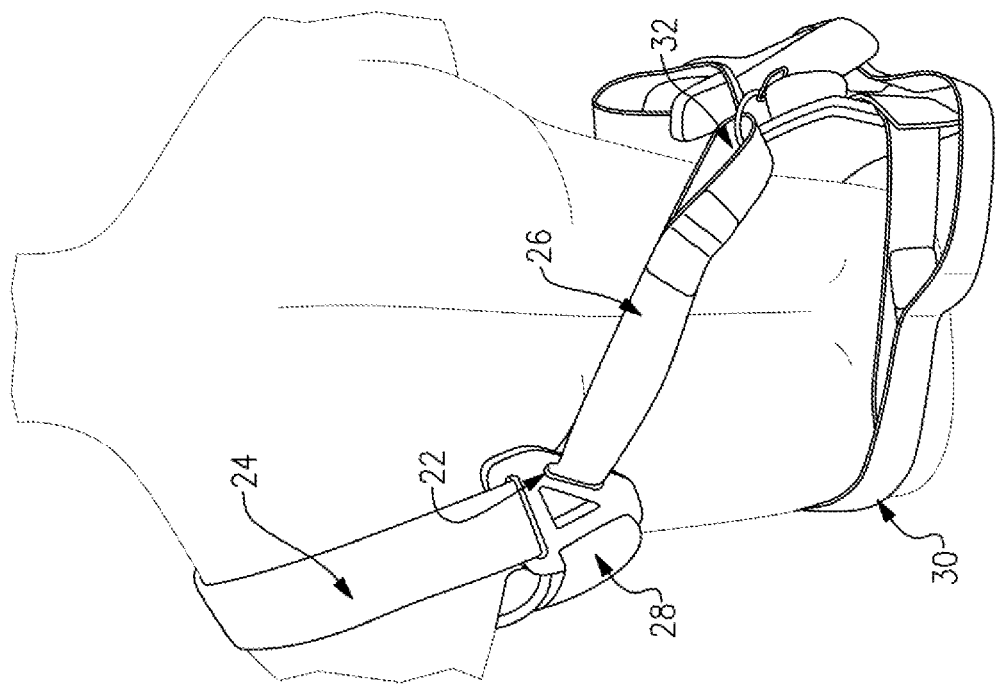
FIG. 1B shows a back perspective view of one implementation of the comfort harness of the present disclosure.

There are many forms of orthoses, or devices used externally to modify the structure and/or function of the skeletal and/or neuromuscular systems of the body. For example, there are orthoses that are applied to the neck, to the spine, to the upper limbs, and to the lower limbs. Additionally, there are many different purposes for using orthoses ranging from rehabilitative to prophylactic. Rehabilitation braces are typically used to limit the movement of a portion of the body following an injury or a surgery.

Certain rehabilitation braces, for example orthopedic arm braces, typically immobilize the arm and/or limit the motion in the shoulder, the elbow and/or the wrist. These braces provide a mechanism to reduce the range of motion for a healing limb. The ability to limit flexion and extension are important features for an effective orthopedic shoulder brace, as are limited abduction and adduction. In certain cases, limiting both internal and external rotation is also important. To maximize the benefits of an orthopedic brace it must be properly fitted and adjusted to the patient. Adjustment variables include fitting patients of various sizes and body proportions, and accommodating a variety of possible surgical or injury sites. The adjustment of the brace will also be continual as the patient heals and can tolerate larger ranges of motion, as swelling is reduced, and the like. At times there may also be readjustment of the braces to adapt to accessories and/or product upgrades.

It is understood that wearing an orthotic brace for an extended period of time can be uncomfortable, and can even lead to additional injuries such as abrasions or strain on other parts of the body, such as the neck or back when wearing an arm immobilizing brace. As noted previously, conventional systems have several drawbacks. Some drawbacks with conventional orthotics are having a single strap located over the shoulder of a user when worn that has no release capability from the user's arm when the user is in a sitting position. There, a single pad over the shoulder does not disperse the load across the user's chest but pulls both straps down to buckle on a sling, for example, and does not anatomically conform to the shape of the user's chest and shoulder area. Conventional single strap and single pad orthotics run over the user's shoulder and place pressure on the user's neck area. A second strap connection that runs horizontally around the waist is used to facilitate immobilization of the user's arm. This design also does not disperse the load across the user's shoulder area and can cause additional injury and discomfort. Although a horizontal waist strap is removable to allow for arm (mobilization), the conventional neck strap is fixed and not removable. Thus, access to the shoulder and arm of the user's carrying side requires the patient to slide their arm out of the orthotic. There, a user cannot be sitting in a chair or lying in bed and easily remove conventional braces.

One implementation of the present disclosure is a comfort harness strap system configured to connect to a multitude of orthotics, or sling designs. In certain implementations, the comfort harness connects to a front and a side portion of a sling. In some cases, the comfort harness covers a multitude of size ranges and has adjustable straps.

The unique adjustability of the present disclosure allows the comfort harness to be universally fit and easily removed. In some implementations, a detachable closure system interfaces with a single "crescent shaped" pad and has two hook and loop removable straps at each end of the pad and a front strap that attached to a fixed ring and has a lower quick connect buckle for attaching to an orthotic. In some implementations, the fixed ring feature allows the front strap to rotate naturally on the single crescent shaped pad which sits anatomically on the chest and shoulder of a user. In one implementation of the comfort harness of the present disclosure the crescent shaped pad can be quickly removed and adjusted while a patient is lying in bed or in a seated position. This facilitates easy access for physician assessment of an injury or removal of the orthotic for postoperative procedures while not increasing patient discomfort.

Figure 1A:
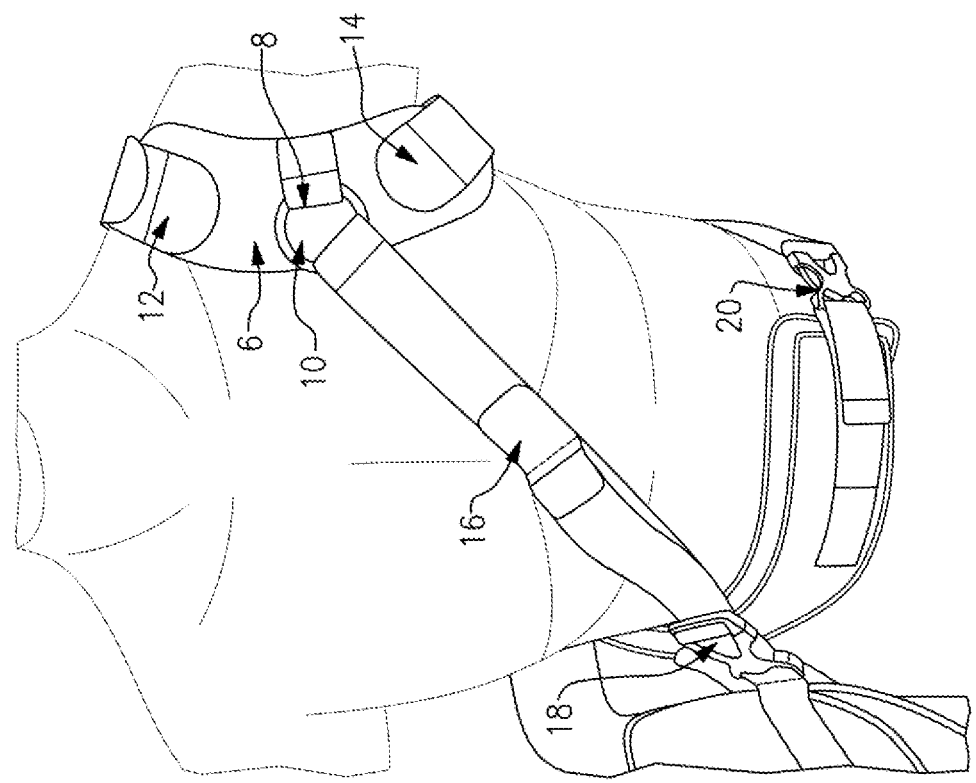
FIG. 1A shows a front perspective view of one implementation of the comfort harness of the present disclosure.

Referring to FIG. 1A, a front perspective view of one implementation of the comfort harness of the present disclosure is shown. More specifically, one implementation of the comfort harness of the present disclosure has a single crescent shaped pad 6 that cradles the front portion of a user's chest/shoulder. In some cases, straps are joined with hook and loop 12, 14 for adjustment over the shoulder (e.g., upper back strap) and under the arm of the user. In some cases, a ring 10, or the like, is fixed 8 to the crescent pad 6 to provide for a cross-body strap 16, which connects to a sling, or other orthotic 4, via a connector 18. In some cases, the cross-body strap 16 is adjustable using hook and loop, or the like, to properly fit a user. In some cases, the orthotic, for which the comfort harness is attached, has a closure 20 to secure the orthotic around the waist of a user. One benefit of the crescent pad 6 is to prevent the d-ring, or the like, from touching the user and causing abrasions. Another benefit of the crescent pad 6 is to disperse the load across a larger region of chest/shoulder for greater comfort.

Referring to FIG. 1B, a back perspective view of one implementation of the comfort harness of the present disclosure is shown. More specifically, an upper back strap 24 (which connects to the upper portion of the crescent pad 6 via hook and loop 12) is also adjustable about a multi-strap connector 22. In some cases, the comfort harness has a custom back pad that is a multi-strap connector 22 for joining an upper back strap 24, a lower back strap 26 (e.g., a second cross-body strap), and an under arm strap 28 that connect to the lower portion of the crescent pad 6 via hook and loop 14. In certain implementations, the lower cross-body back strap 26 connects to a sling 4, or other orthotic via a connector 32.

Figure 2:
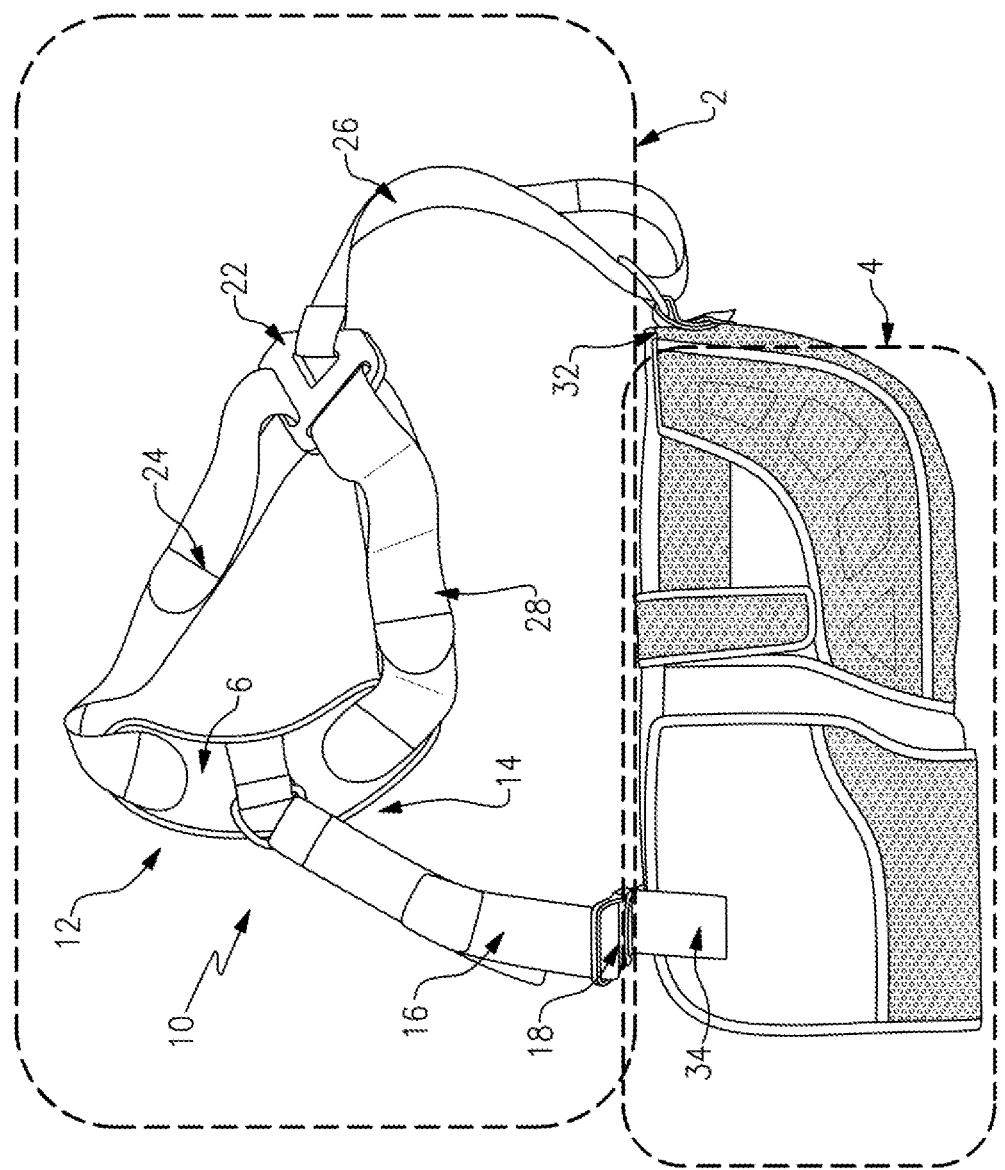
FIG. 2 shows a perspective view of one implementation of the comfort harness for an orthotic brace according to the principles of the present disclosure.

Referring to FIG. 2, a perspective view of one implementation of the comfort harness for an orthotic brace according to the principles of the present disclosure is shown. More specifically, a sling, or orthotic 4, is used in conjunction with the comfort harness 2 of the present disclosure. On benefit of the comfort harness of the present disclosure is that the straps are easily removable from the front of a user when donned, allowing a user to be in a chair or bed and have the various straps removed for added comfort and to minimize further injury. Additionally, the comfort harness design of the present disclosure keeps the straps away from the user's neck where it could rub of chafe.

Still referring to FIG. 2, certain implementations of the comfort harness 2 attach to an orthotic via connectors 18 and 32. A crescent-shaped pad 6 and a multi-strap connector 22 provide for attachment of an under arm strap 28, a front cross-body strap 16, an upper back strap 24, and a lower cross-body back strap 26. Each of these straps (16, 24, 26, 28) are adjustable via hook and loop, or the like, for accurately, and comfortably fitting a variety of different sized users. In certain implementations, the cross-body straps 16, 26 are made of non-stretching fabric. In certain implementations, the under arm 28 and upper back strap 24 straps that connect to the lower and the upper portions of the single pad 6, respectively, are made non-stretching fabric. In certain implementations, the under arm 28 and upper back strap 24 straps that connect to the lower and the upper portions of the single pad 6, respectively, are made of stretchable fabric. In some implementations, the multi-strap connector 22 is formed of LDPE/foam plastic, or the like. In some cases, the multi-strap connector 22 is injection molded.

Figure 3:
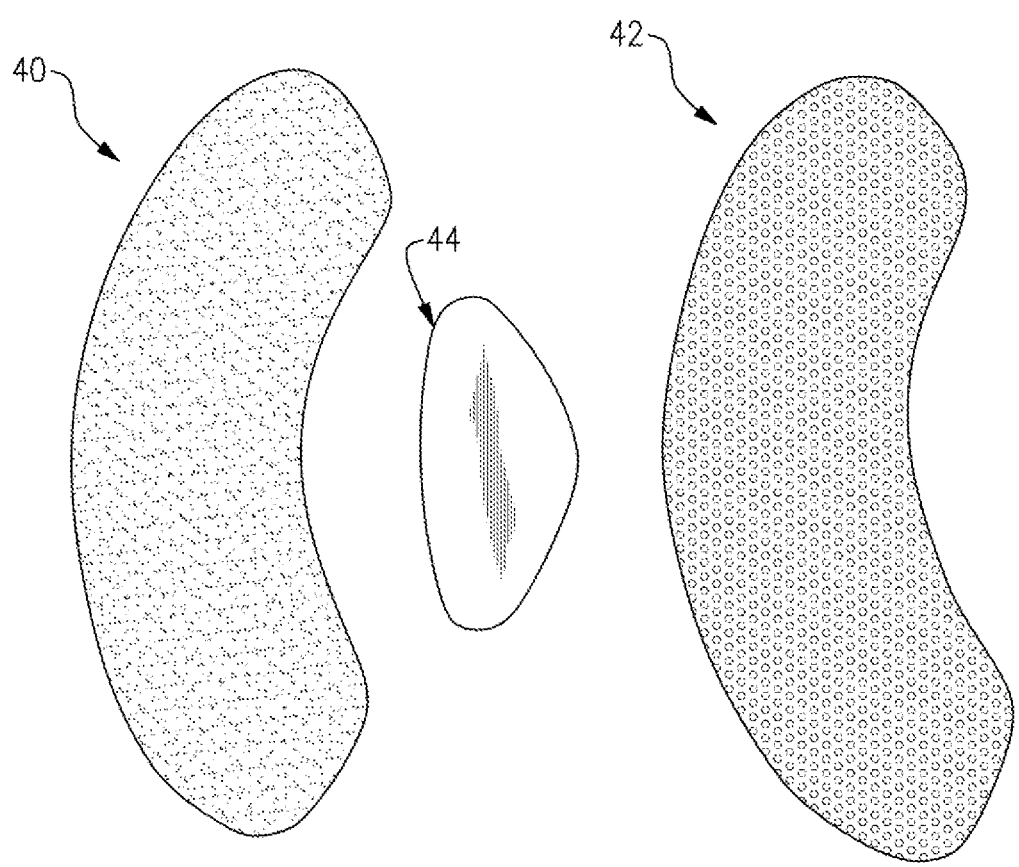
FIG. 3 shows an exploded view of one implementation of a crescent portion of a comfort harness for an orthotic brace according to the principles of the present disclosure.

Referring to FIG. 3, an exploded view of one implementation of a single crescent shaped pad of a comfort harness for an orthotic brace according to the principles of the present disclosure is shown. More specifically, in one implementation a single top layer 40 comprises loop laminate and faces away from a user when worn and a single bottom layer 42 facing toward a user's body when worn. The single bottom layer being sized and shaped to match the top layer. In certain implementations, the single bottom layer comprises soft foam laminate. In other cases, the single bottom layer further comprises mesh with a cooling fabric, or the like for added comfort against the user's body. In some implementations, a single rigid middle layer 44 reinforces the single pad to prevent distortion when the comfort harness is under tension. In one implementation the rigidity is due to being made of LDPE. In one implementation, the rigid middle layer is sandwiched between the top and bottom layer and is so smaller dimensions. In some cases, the single rigid middle layer is approximately triangular.

Figure 4B:
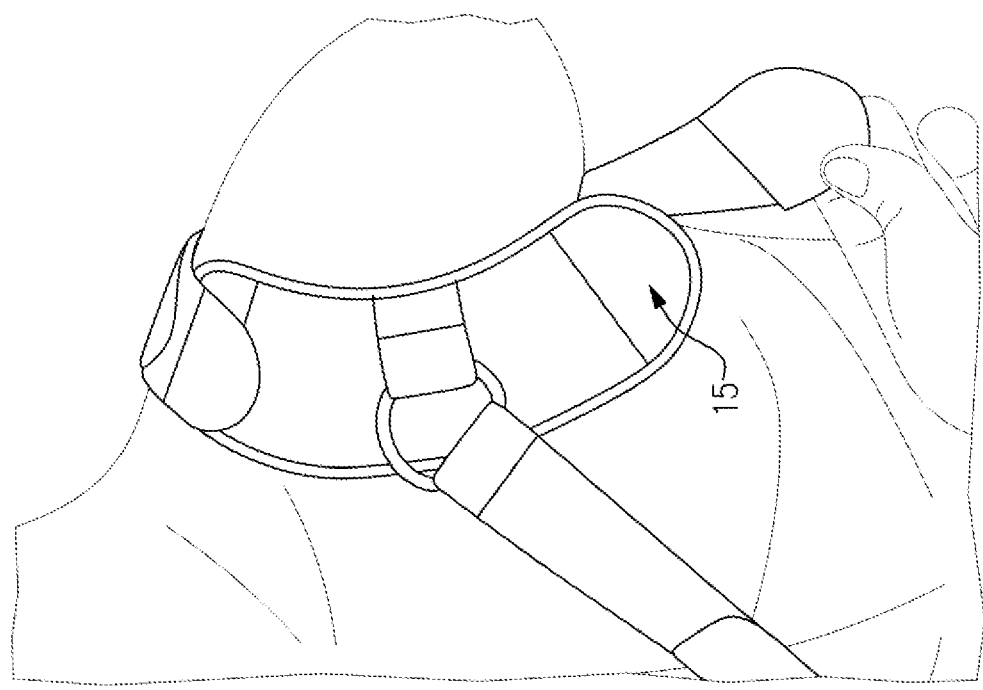
FIG. 4B shows a second front perspective view of one implementation of a crescent portion of a comfort harness for an orthotic brace according to the principles of the present disclosure.
Figure 4A:
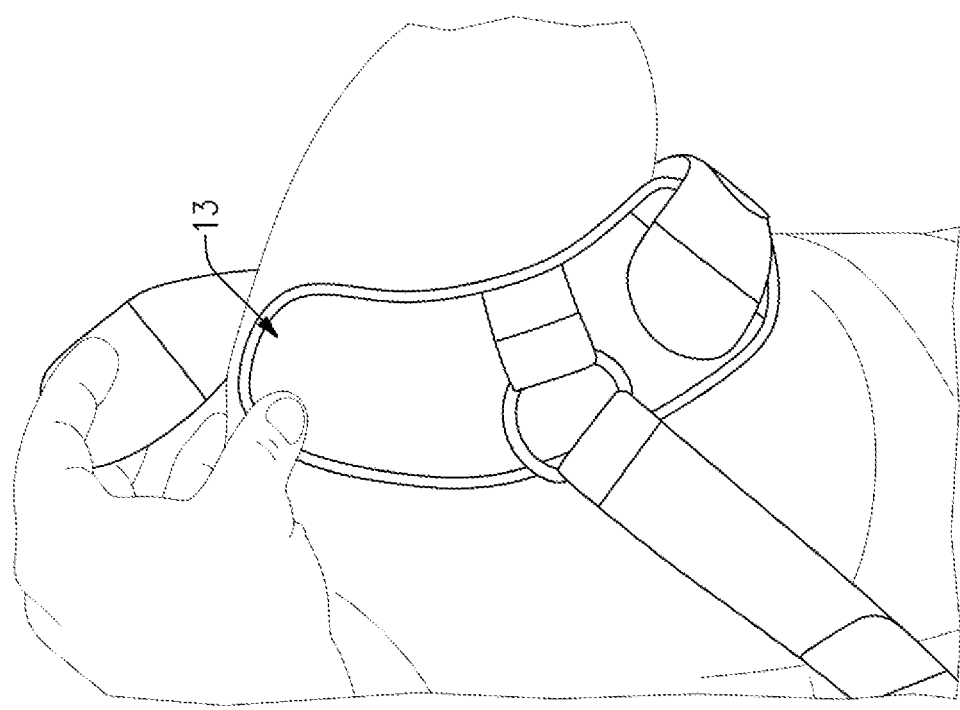
FIG. 4A shows a first front perspective view of one implementation of a crescent portion of a comfort harness for an orthotic brace according to the principles of the present disclosure.

Referring to FIG. 4A, a first front perspective view of one implementation of a single crescent pad of a comfort harness for an orthotic brace according to the principles of the present disclosure is shown. More specifically, the crescent shaped pad 6 is adjustable at a top portion 13. This provides for comfort adjustment and ease of use for a user. This is particularly true when the user is sitting in a chair or lying down, the harness can be adjusted or even disconnected easily by the user.

Referring to FIG. 4B, a second front perspective view of one implementation of a crescent portion of a comfort harness for an orthotic brace according to the principles of the present disclosure is shown. More specifically, the crescent shaped pad is adjustable at a bottom portion 15. This also provides for comfort adjustment and ease of use for a user. This is particularly true when the user is sitting in a chair or lying down, the harness can be adjusted or even disconnected easily by the user.

Figure 5B:
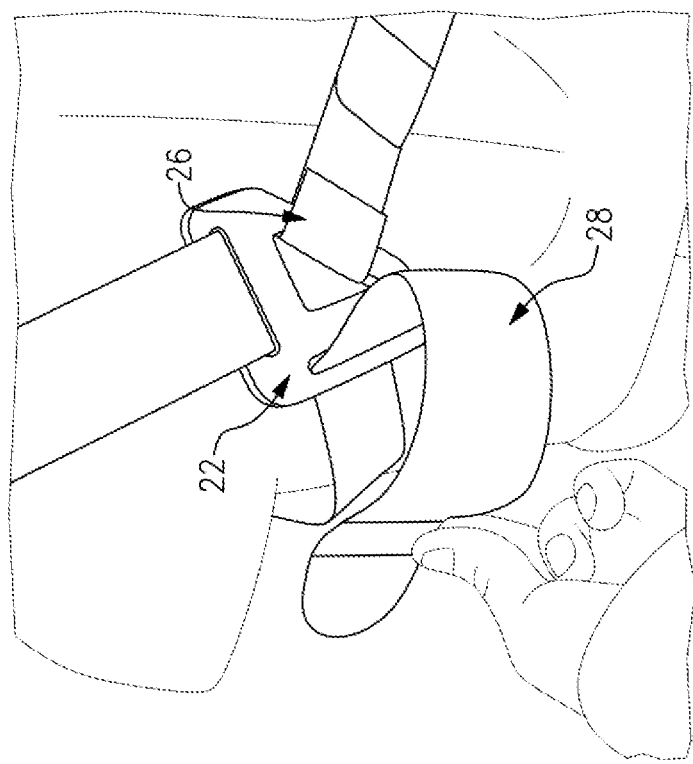
FIG. 5B shows a second back perspective view of one implementation of a connector portion of a comfort harness for an orthotic brace according to the principles of the present disclosure.
Figure 5A:
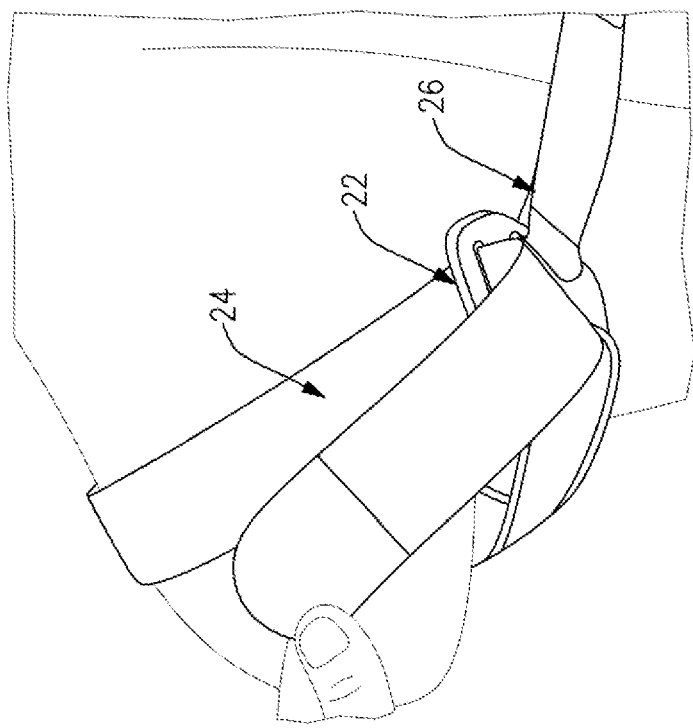
FIG. 5A shows a first back perspective view of one implementation of a connector of a comfort harness for an orthotic brace according to the principles of the present disclosure.

Referring to FIG. 5A, a first back perspective view of one implementation of a connector of a comfort harness for an orthotic brace according to the principles of the present disclosure is shown. More specifically, an upper back strap 24 is fully adjustable about a multi-strap connector 22 in reference to the other straps, including a cross-body back strap 26. Referring to FIG. 5B, a second back perspective view of one implementation of a connector portion of a comfort harness for an orthotic brace according to the principles of the present disclosure is shown. More specifically, an under arm strap 28 is fully adjustable in relation to the multi-strap connector 22 in relation to the other straps, including a cross-body back strap 26. One benefit of this implementation of the comfort harness is that the multi-strap connector pad in the back of the user, when worn, is designed for comfort (e.g., semi-flexible) and a low profile fit.

Figure 6:
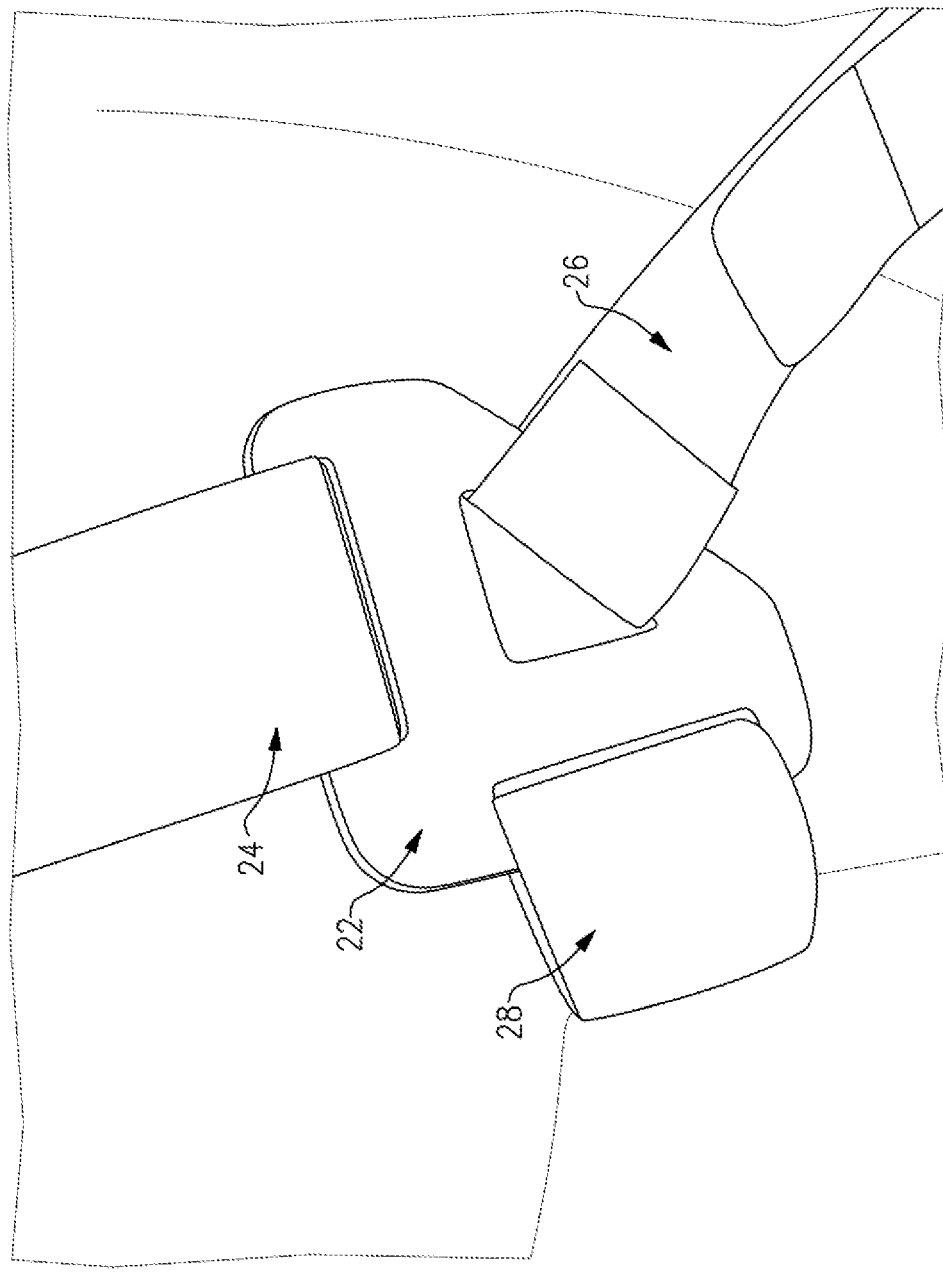
FIG. 6 shows a third back perspective view of one implementation of a connector portion of a comfort harness for an orthotic brace according to the principles of the present disclosure.

Referring to FIG. 6, a third back perspective view of one implementation of a multi-strap connector portion of a comfort harness for an orthotic brace according to the principles of the present disclosure is shown. More specifically, a multi-strap connector 22 is proportioned to accommodate multiple straps. In some cases there are three straps reversibly connected to the connector 22 via hook and loop, or the like. In some implementations there are three straps 24, 26, 28. In some cases some or all of the straps are constructed of stretchable materials. In some cases one or more of the straps are permanently connected to the multi-strap connector. In some cases, the strap material is not stretchable.

Referring to FIG. 7A, a perspective view of one implementation of the comfort harness for an orthotic brace having strap pads according to the principles of the present disclosure is shown. More specifically, in some cases one or more strap pads 30 are used to surround one or more of the straps in the comfort harness to provide for additional comfort for the user when work. In certain implementations, the one or more strap pads 30 comprise foam laminate. In some implementations, the one or more strap pads 30 are secured at one end using a connection tab 32 having a hook interaction (e.g., hook/loop), or the like, to attach to an end of the crescent shaped pad 6. The strap connection region 12 is also shown. Referring to FIG. 7B, one implementation of a strap pad is a tube-like strap pad 30 that is installed over a strap and has a connection tab 32, or the like, on at least one end.

Referring to FIG. 8A, a perspective view of one implementation of the comfort harness for an orthotic brace having one or more strap pads and a fixed ring according to the principles of the present disclosure is shown. More specifically, in some cases, the fixed ring is a double bar D-ring 10. Referring to FIG. 8B, the fixed ring 10 is secured 8 along the convex edge of the single pad 6. In some cases, the fixed ring is sewn or otherwise fixed to the pad. In one implementation of the comfort harness of the present disclosure, a pair of strap pads 30 are reversibly attachable to the single pad 6 using connection tabs 32, or the like. This secures the strap pads such that they will not move along the length of the strap when worn by a user and therefore will help to minimize chafing.

While various implementations of the present disclosure have been described in detail, it is apparent that various modifications and alterations of those implementations will occur to and be readily apparent to those skilled in the art. However, it is to be expressly understood that such modifications and alterations are within the scope and spirit of the present disclosure, as set forth in the appended claims. Further, the disclosure(s) described herein is capable of other implementations and of being practiced or of being carried out in various other related ways. In addition, it is to be understood that the phraseology and terminology used herein is for the purpose of description and should not be regarded as limiting. The use of "including," "comprising," or "having," and variations thereof herein, is meant to encompass the items listed thereafter and equivalents thereof as well as additional items while only the terms "consisting of" and "consisting only of" are to be construed in a limitative sense.

The foregoing description of the implementations of the present disclosure has been presented for the purposes of illustration and description. It is not intended to be exhaustive or to limit the present disclosure to the precise form disclosed. Many modifications and variations are possible in light of this disclosure. It is intended that the scope of the present disclosure be limited not by this detailed description, but rather by the claims appended hereto.

A number of implementations have been described. Nevertheless, it will be understood that various modifications may be made without departing from the scope of the disclosure. Although operations are depicted in the drawings in a particular order, this should not be understood as requiring that such operations be performed in the particular order shown or in sequential order, or that all illustrated operations be performed, to achieve desirable results.

While the principles of the disclosure have been described herein, it is to be understood by those skilled in the art that this description is made only by way of example and not as a limitation as to the scope of the disclosure. Other implementations are contemplated within the scope of the present disclosure in addition to the exemplary implementations shown and described herein. Modifications and substitutions by one of ordinary skill in the art are considered to be within the scope of the present disclosure.

What is claimed:

1. A comfort harness for an orthotic, comprising:
a single pad comprising
an upper rounded end portion located between a user's neck and a user's shoulder when worn;
a middle portion located over a user's pectoral muscle when worn supporting a fixed ring, the fixed ring being configured to connect to at least one cross-body strap;
a lower rounded end portion located proximal to a user's arm pit when worn; and
a pair of parallel curves extending between the upper rounded portion and the lower rounded portion such that the single pad has an equal width from end to end, a first parallel curve forming a convex edge located adjacent a user's chest when worn, and a second parallel curve forming a concave edge located spaced away from a user's shoulder when worn;
the upper rounded end portion reversibly attachable to an upper back strap and the lower rounded end portion reversibly attachable to an under arm strap;
the single pad further comprising:
a single top layer facing away from a user's body when worn;
a single bottom layer facing toward a user's body when worn, the single bottom layer being sized and shaped to match the top layer; and
a rigid single middle layer that is sandwiched between the single top layer and the single bottom layer; and
a multi-strap connector located on a back of a user when worn having two or more slots for receiving and orienting straps and reversibly attachable to the upper back strap and the under arm strap;
the at least one cross-body strap being reversibly attachable to an orthotic.

2. The comfort harness according to claim 1, wherein the at least one cross-body strap comprises a first and a second cross-body strap.

3. The comfort harness according to claim 2, wherein the first cross-body strap is reversibly attached to the fixed ring on the single pad and reversibly attached to the orthotic.

4. The comfort harness according to claim 3, wherein the second cross-body strap is permanently attached to the multi-strap connector and reversibly attached to the orthotic.

5. The comfort harness according to claim 1, further comprising at least one strap pad sized to fit around the upper back strap and/or the under arm strap.

6. The comfort harness according to claim 5, wherein the at least one strap pad is a pair of strap pads each made of foam laminate and having a tab for reversibly securing to the single pad.

7. The comfort harness according to claim 1, wherein the single pad further comprises cooling fabric.

8. A comfort harness for an orthotic, comprising:
a single pad comprising:
an upper rounded end portion located between a user's neck and a user's shoulder when worn;
a middle portion supporting a fixed ring located over a user's pectoral muscle when worn;
a lower rounded end portion located proximal to a user's arm pit when worn; and
a pair of parallel curves such that the single pad has an equal width from end to end, a first parallel curve forming a convex edge located adjacent a user's chest when worn, and a second parallel curve forming a concave edge located spaced away from a user's shoulder when worn;
the upper rounded end portion reversibly attachable to an upper back strap and the lower rounded end portion reversibly attachable to an under arm strap,
the single pad comprising:
a single top layer of loop laminate facing away from a user's body when worn;
a single bottom layer facing toward a user's body when worn; and
a single middle layer enclosed within the single top layer and the single bottom layer to reinforce the single pad and prevent distortion when the harness is under tension; and
a multi-strap connector comprising at least two slots for receiving straps, the multi-strap connector reversibly attachable to at least the upper back strap and the under arm strap;
wherein a first cross-body strap is reversibly attached to the fixed ring on the single pad and reversibly attached to an orthotic and a second cross-body strap is reversibly attachable to the orthotic.

9. The comfort harness according to claim 8, further comprising at least one strap pad sized to fit around the upper back strap and/or the under arm strap.

10. The comfort harness according to claim 9, wherein the at least one strap pad is a pair of strap pads each made of foam laminate and having a tab for reversibly securing to the single pad.

11. The comfort harness according to claim 8, wherein the orthotic is a sling.

12. The comfort harness according to claim 8, wherein the second cross-body strap is permanently attached to the multi-strap connector and reversibly attached to the orthotic.

13. The comfort harness according to claim 8, wherein the single pad further comprises cooling fabric.

14. A comfort harness for an arm orthotic, comprising:
a single pad having
an upper rounded end portion located between a user's neck and a user's shoulder when worn;
a middle portion having a fixed ring for receiving a first cross-body strap and located over a user's pectoral muscle when worn;
a lower rounded end portion located proximal to a user's arm pit when worn; and
a pair of parallel curves such that the single pad has an equal width from end to end, a first parallel curve forming a convex edge located adjacent a user's chest when worn, and a second parallel curve forming a concave edge located spaced away from a user's shoulder when worn;
the upper rounded end portion being reversibly attachable to an upper back strap and the lower rounded end portion reversibly attachable to an under arm strap,
the single pad comprising:
a top layer comprising loop laminate facing away from a user's body when worn;
a bottom layer comprising foam laminate facing toward a user's body when worn; and a rigid single middle layer that is sandwiched between the top layer and the bottom layer to prevent distortion when the harness is under tension; and a multi-strap connector having two or more slots for receiving and orienting straps on a back of the user and reversibly attachable to the upper back strap and the under arm strap.

15. The comfort harness according to claim 14, further comprising at least one strap pad sized to fit around the upper back strap and/or the under arm strap.

16. The comfort harness according to claim 15, wherein the at least one strap pad is a pair of strap pads each made of foam laminate and having a tab for reversibly securing to the single pad.

17. The comfort harness according to claim 14, wherein the first cross-body strap is reversibly attached to the fixed ring on the single pad and reversibly attached to the arm orthotic.

18. The comfort harness according to claim 14, further comprising a second cross-body strap permanently attached to the multi-strap connector and reversibly attached to the arm orthotic.

19. The comfort harness according to claim 14, wherein the single pad further comprises cooling fabric.

20. The comfort harness according to claim 14, wherein the fixed ring is located at the convex edge of the middle portion of the single pad.

\* \* \* \* \*